US012588940B2

(12) United States Patent
    Dijkstra

(10) Patent No.: US 12,588,940 B2
(45) Date of Patent: Mar. 31, 2026

(54) TESTING DEVICE FOR AN ELECTROSURGICAL GENERATOR

(71) Applicant: OLYMPUS WINTER & IBE GMBH, Hamburg (DE)

(72) Inventor: Jelle Dijkstra, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 1086 days.

(21) Appl. No.: 16/979,664

(22) PCT Filed: Feb. 16, 2019

(86) PCT No.: PCT/EP2019/053907
    § 371 (c)(1),
    (2) Date: Sep. 10, 2020

(87) PCT Pub. No.: WO2019/174859
    PCT Pub. Date: Sep. 19, 2019

(65) Prior Publication Data
    US 2021/0022793 A1      Jan. 28, 2021

(30) Foreign Application Priority Data
    Mar. 13, 2018    (DE) ..................... 10 2018 105 824.1

(51) Int. Cl.
    *A61B 18/12*        (2006.01)
    *A61B 18/00*        (2006.01)
(52) U.S. Cl.
    CPC ..................... *A61B 18/1206* (2013.01); *A61B 2018/00178* (2013.01); *A61B 2018/00702* (2013.01); *A61B 2018/0094* (2013.01)

(58) Field of Classification Search
    CPC ...... A61B 18/1206; A61B 2018/00178; A61B 2018/00702; A61B 2018/0094
    See application file for complete search history.

(56) References Cited

U.S. PATENT DOCUMENTS

| 5,133,711 A | * | 7/1992 | Hagen ................ A61B 18/1206 |
| | | | 606/38 |
| 6,142,992 A | | 11/2000 | Cheng et al. |

(Continued)

FOREIGN PATENT DOCUMENTS

| DE | 10 2004 010 769 A1 | 9/2005 |
| EP | 0 391 233 A2 | 10/1990 |

(Continued)

OTHER PUBLICATIONS

Jun. 26, 2019 International Search Report with English Translation issued in PCT/EP/2019/053907.

(Continued)

*Primary Examiner* — Michael F Peffley
*Assistant Examiner* — Bo Ouyang
(74) *Attorney, Agent, or Firm* — Oliff PLC

(57) ABSTRACT

A testing device for an electrosurgical generator, including a first connection port and a second connection port for connecting the testing device to a patient circuit of the electrosurgical generator and including an apparatus for producing a direct voltage between the first connection port and the second connection port. The testing device is characterized in that an HF current path of the patient circuit, running from the first connection port to the second connection port, extends through the testing device and in that the apparatus for producing a direct voltage is fed by an HF current flowing through the HF current path.

13 Claims, 3 Drawing Sheets

(56)           References Cited

U.S. PATENT DOCUMENTS

Figure 1:
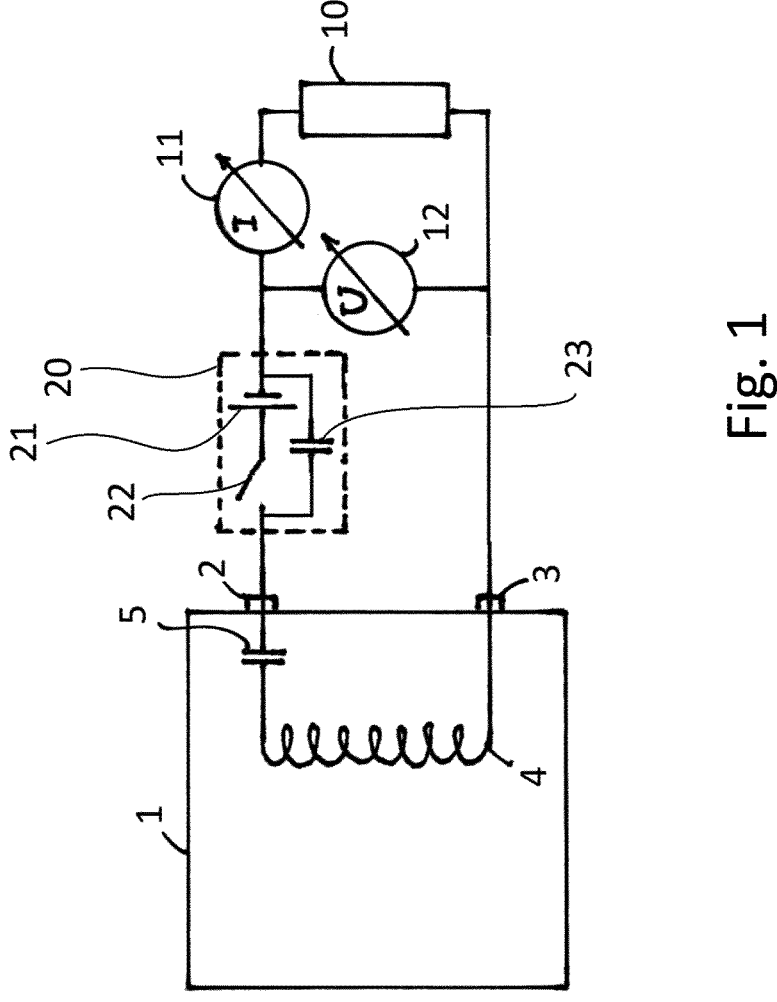

| 2005/0182398 | A1 * | 8/2005  | Paterson  | ............ | A61B 18/1233 |
|              |      |         |           |              | 606/34       |
| 2010/0312239 | A1 * | 12/2010 | Sclig     | ...................... | A61B 18/16 |
|              |      |         |           |              | 606/35       |
| 2013/0110103 | A1 * | 5/2013  | Assmus    | ................. | A61B 18/12 |
|              |      |         |           |              | 606/37       |
| 2013/0345696 | A1 * | 12/2013 | Behnke, II | ......... | A61B 18/1206 |
|              |      |         |           |              | 606/34       |
| 2014/0086273 | A1 * | 3/2014  | Gliner    | ............... | A61B 18/1492 |
|              |      |         |           |              | 374/1        |

FOREIGN PATENT DOCUMENTS

| EP | 0 750 382 A2 | 12/1996 |
| EP | 2 468 359 B1 | 10/2014 |

OTHER PUBLICATIONS

Jun. 26, 2019 International Search Report issued in International patent Application No. PCT/EP2019/053907.

* cited by examiner

TESTING DEVICE FOR AN ELECTROSURGICAL GENERATOR

The invention relates to a testing device for an electrosurgical generator, having a first connection port and a second connection port for connecting the testing device to a patient circuit of the electrosurgical generator, and having a unit for generating a DC voltage between the first connection port and the second connection port.

Electrosurgical generators are used in modern medicine for a wide variety of purposes. Between two connection ports, the electrosurgical generator generates a high-frequency alternating current or HF current which is applied by means of an instrument to be connected to the electrosurgical generator in a tissue to be treated. The frequency of said HF current is usually between 100 kHz and 500 kHz, but electrosurgical generators, which operate in the frequency range of up to 5 MHz, are also known.

In order to safely avoid unwanted current flows, the high-frequency alternating current is provided in an electrically isolated patient circuit.

The instruments to be connected are either monopolar or bipolar instruments. Monopolar instruments are connected to only one connection port of the electrosurgical generator; in such case, the patient circuit is closed via an application electrode of the instrument and a neutral electrode which is connected to a large area of a body surface of the patient and which is connected to the second connection port of the electrosurgical generator. Bipolar instruments, on the other hand, are connected to both connection ports of the electrosurgical generator; they have two application electrodes.

When the HF current is applied, an intentional or unintentional sparking between an application electrode and the tissue to be treated or a further application electrode can occur. Such sparking must be reliably recognized by the electrosurgical generator.

Sparking leads to an asymmetrical course of the current flow through the patient circuit. For example, the current flow in positive half-waves of the HF current can be reduced in comparison to the current flow in negative half-waves of the HF current. This asymmetrical course of the current flow leads to a DC component being superimposed over the HF current, which, however, is not permitted for reasons of patient safety.

In order to suppress this DC component, a capacitor is integrated in the patient circuit. Due to the asymmetrical current flow, a DC voltage builds up across said capacitor as soon as a spark ignites in the patient circuit. This DC voltage is recognized by the control of the electrosurgical generator. Depending on the desired treatment effect, the control can then adjust the HF current such that the spark is either suppressed or maintained in a controlled manner. In individual operating modes of an electrosurgical generator, it is also possible to switch between individual phases of a treatment when the sparking is detected.

In order to check the correct functioning of an electrosurgical generator, it must be subjected to a function test. The characteristic values of the output HF current are determined in all available operating modes of the electrosurgical generator, and the correct sequence of the treatment phases is checked.

For this purpose, the correct detection of the sparking and the corresponding reaction of the electrosurgical generator must also be checked. Actual sparking only occurs in conjunction with real tissue and is therefore difficult to realize in the test sequence.

Therefore, testing devices of the type in question are used for checking the spark detection of electrosurgical generators. They simulate the generation of sparks by applying a DC voltage in the patient circuit of the electrosurgical generator, which corresponds approximately to the DC voltage resulting from sparking.

For this purpose, known testing devices have an external power supply, from which the unit for generating the DC voltage is fed. In this case, the DC voltage is applied in series to an HF current path, in which, for example, measuring instruments for current strength, voltage and/or power of the emitted HF current are arranged.

However, there are various problems. The generation of the DC voltage can be difficult to synchronize with the emission of the HF current by the electrosurgical generator, for example, in operating modes with rapidly successive treatment phases. The complexity of the test setup is also further increased by the required power supply of the testing device.

Therefore, the problem addressed by the invention is that of providing a testing device for electrosurgical generators which is improved with regard to the problems described.

According to the invention, this problem is solved by a testing device for an electrosurgical generator, having a first connection port and a second connection port for connecting the testing device to a patient circuit of the electrosurgical generator, and having a unit for generating a DC voltage between the first connection port and the second connection port, characterized in that an HF current path of the patient circuit runs from the first connection port to the second connection port through the testing device, and that the unit for generating a DC voltage is fed by an HF current flowing through the HF current path.

As a result of this measure, the DC voltage generated in the testing device is automatically synchronized with the HF current generated by the electrosurgical generator, i.e., it is built up precisely when the electrosurgical generator emits HF current. At the same time, an external power supply for the testing device is unnecessary, which considerably simplifies the test setup.

In one possible embodiment of the invention, the unit for generating a DC voltage can comprise a capacitor which is arranged in the HF current path. In such case, the DC voltage can be generated by charging the capacitor, wherein the HF current is simultaneously barely influenced if the capacitor is appropriately dimensioned.

According to a development of the invention, the unit for generating a DC voltage can be designed to conduct positive half-waves of the HF current through the capacitor and to not conduct negative half-waves of the HF current through the capacitor. The capacitor is thus charged by the positive half-waves of the HF current without being discharged again by the negative half-waves.

The terms "positive half-wave" and "negative half-wave" take into account the fact that the direction of current changes periodically with an alternating current. Here, the section of the current flow, in which the current flows in a first direction is called the "positive half-wave," and the section, in which the current flows in the opposite direction is called the "negative half-wave." The selection as to which section is called the positive half-wave is arbitrary. The term "half-wave" is also used for asymmetrical alternating currents and does not imply that opposite half-waves correspond in certain parameters, such as time duration, amplitude, signal form, or the like.

In a preferred implementation of a testing device according to the invention, the unit for generating a DC voltage can have two parallel HF current paths, wherein a first HF current path comprises the capacitor and has a first diode which is polarized in the direction of the positive half-waves of the HF current, and wherein a second HF current path has a second diode which is polarized in the direction of the negative half-waves of the HF current. In this way, the separation of the half-waves of the HF current can be achieved particularly easily.

A testing device according to the invention can have a switch in the first HF current path for bridging the first diode. By closing the switch, the rectifying effect of the first diode is canceled out, so that both half-waves of the HF current can flow through the capacitor, and the capacitor is thus no longer being charged.

All electrically controllable switches, e.g., relays, are suitable as switches in the sense of the invention. However, transistors are preferably used here, e.g., MOSFETs.

According to a particularly preferred embodiment of a testing device according to the invention, the unit for generating a DC voltage is designed to close the first switch when the DC voltage across the capacitor reaches a predetermined or predeterminable value. In this way, the generated DC voltage can be limited to a value that would normally occur in the event of sparking. This value can be, for example, between 5V and 300V, preferably between 50V and 200V, preferably between 80V and 170V, and particularly preferably between 100V and 150V.

In a further possible embodiment of the invention, the testing device can have a device for discharging the capacitor. By means of such a device, the DC voltage can be quickly reduced or completely dissipated by discharging the capacitor.

The device for discharging the capacitor can advantageously be designed to discharge the capacitor when no HF current flows through the HF current path. As a result, the extinguishing of a spark by switching off the HF current can be simulated.

In a preferred embodiment of the invention, the device for discharging the capacitor can comprise a second switch. This can also be a MOSFET.

Figure 2:
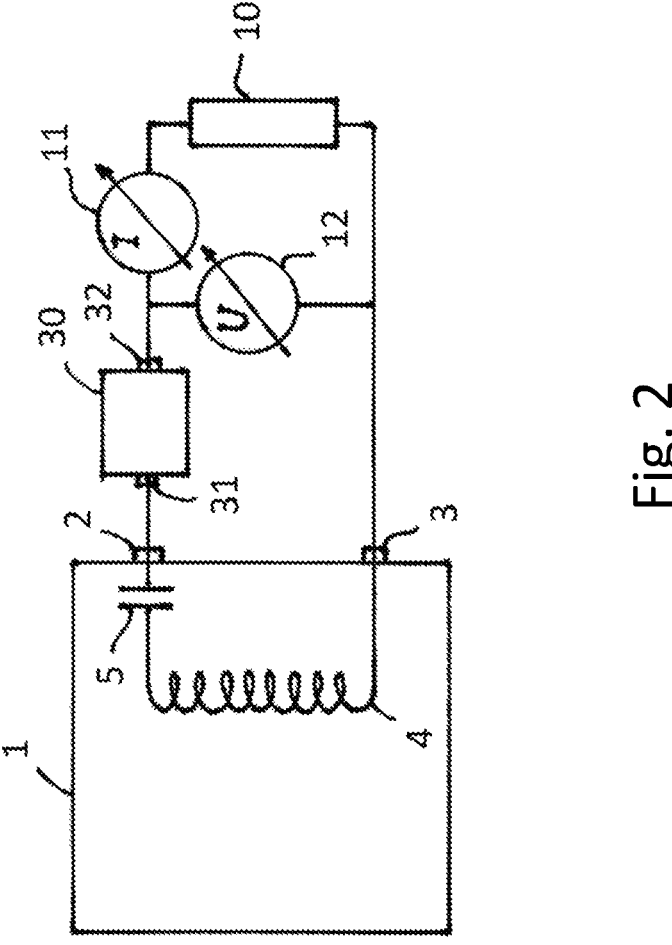
Figure 3:
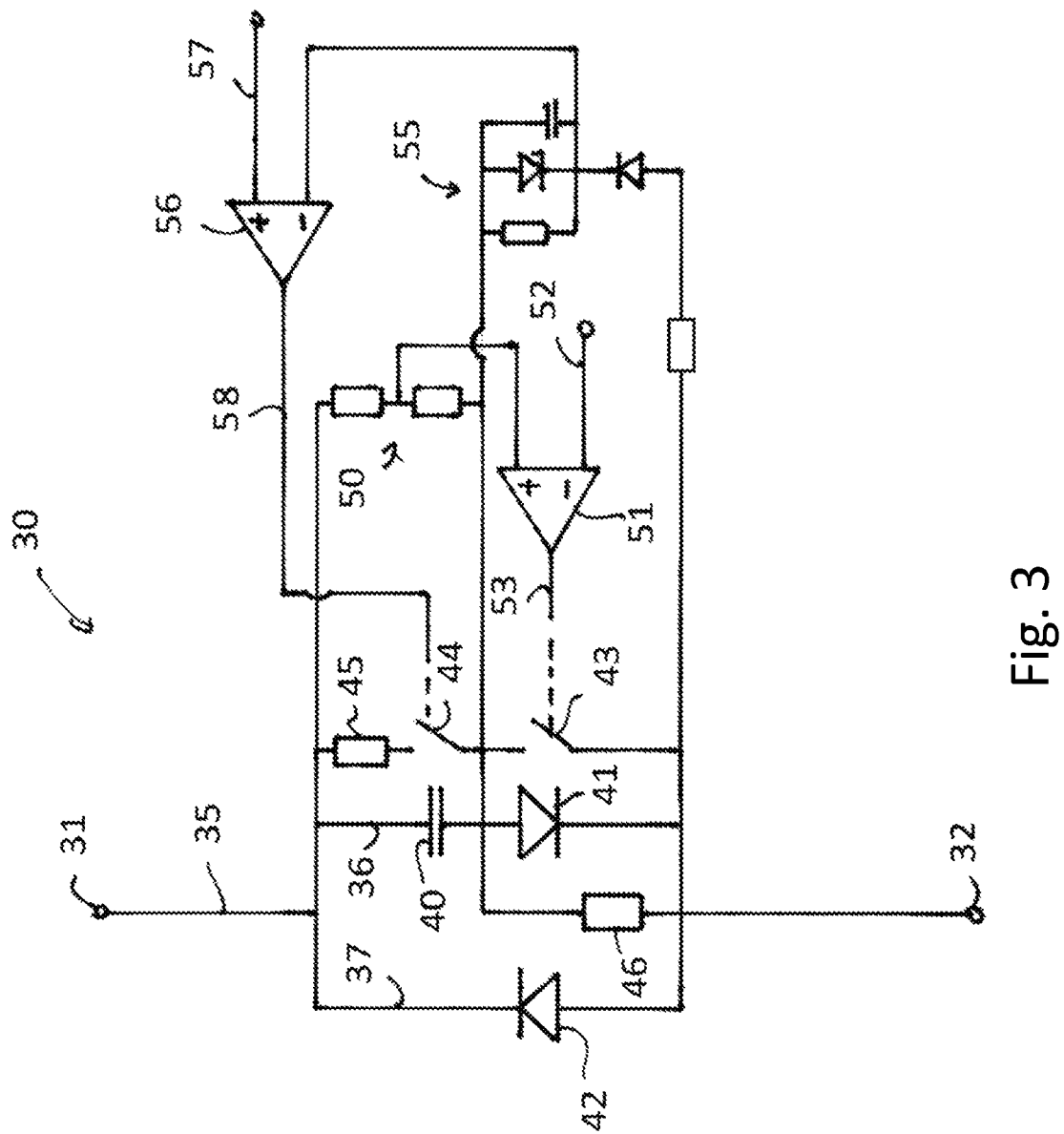

In the following, the invention shall be explained in more detail using some exemplary representations. It is shown in:

FIG. 1: An electrosurgical generator with a connected testing device according to the prior art;

FIG. 2: An electrosurgical generator with a connected testing device according to the invention;

FIG. 3: The basic design of a testing device according to the invention.

FIG. 1 shows an electrosurgical generator 1. The electrosurgical generator 1 comprises connection ports 2, 3 which are part of a patient circuit. The patient circuit is electrically isolated from the power supply (not depicted) of the electrosurgical generator 1, which is indicated by a transformer coil 4. A capacitor 5 suppresses DC components in the patient circuit.

During normal operation of the electrosurgical generator 1, an electrosurgical instrument (not depicted) and possibly a neutral electrode can be connected to the connection ports 2, 3.

FIG. 1 shows the electrosurgical generator 1 in a test configuration. In order to test the correct functioning of the electrosurgical generator 1, a test circuit with a load resistor 10 is connected to the connection ports 2, 3. The HF current emitted by the electrosurgical generator 1 and the voltage drop across the load resistor 10 are measured and logged by the measuring devices 11, 12.

A testing device 20 is integrated in the test circuit in order to simulate a DC voltage that arises in the patient circuit when sparking occurs. The testing device 20 comprises a DC voltage source 21 and a switch 22, via which the DC voltage can be switched on and off. A capacitor 23 is connected in parallel to the DC voltage source 21 and the switch 22 in order to conduct the HF current emitted by the generator 1 through the testing device 20.

FIG. 2 also shows the electrosurgical generator 1, which is connected to a test circuit with a load resistor 10. The measuring devices 11, 12 are also shown.

Instead of the testing device 20, a testing device 30, which is designed according to the invention, with connection ports 31, 32 is integrated into the patient circuit of the electrosurgical generator 1. The internal structure of the testing device 30 is shown in FIG. 3.

FIG. 3 shows the basic electronic structure of the testing device 30. An HF current path 35 extends between the connection ports 31, 32. The HF current path branches into two parallel HF current paths 36, 37. The first HF current path 36 comprises a capacitor 40 and a first diode 41, the second current path 37 comprises a second diode 42.

The diodes 41, 42 are polarized in opposite directions, so that positive half-waves of an HF current flowing through the testing device 30 must flow through the first current path 36 with the capacitor 40, thereby charging the capacitor 40. In contrast, negative half-waves of the HF current flow through the second current path 37.

As a result of this design, the HF current flowing through the capacitor 40 is highly asymmetrical, so that a DC voltage builds up across the capacitor. Said DC voltage is also applied between the connection ports 31, 32 and is therefore visible to the electrosurgical generator 1.

As soon as the DC voltage has reached a predetermined or predeterminable value across the capacitor 40, the diode 41 can be bridged by closing a switch 43. Both half-waves of the HF current can thus flow through the HF current path 37, and the capacitor 40 is no longer being charged.

A second switch 44 is used to discharge the capacitor 40 in a controlled manner via a resistor 45. The resistor 45 is dimensioned such that the capacitor 40 is discharged in a few milliseconds.

A further resistor 46 is parallel-connected to the diode 41 and is used to allow for a potential equalization with the capacitor 5 in the electrosurgical generator 1 during the no-pulse periods in the pulsed operating modes of the electrosurgical generator 1. The RC element consisting of capacitor 40 and resistor 46 has such a large time constant that it is insignificant for the HF current.

As already indicated, the DC voltage generated in the testing device 30 is controlled by means of the switch 43 which is realized as a MOSFET. The DC voltage applied across the capacitor 40 is applied to the positive input of a comparator 51 via a voltage divider 50. A fixed reference voltage 52 is applied to the negative input of the comparator 51. The output 53 of the comparator 51 is connected to the gate of the switch 43.

If the output voltage of the voltage divider 50 reaches the reference voltage 52, the comparator 51 switches and the switch 43 is closed. As a result, the capacitor 40 is no longer being charged.

Since the capacitor 40 slowly discharges via the resistor 46 and the voltage divider 50, the output voltage of the voltage divider 50 will soon fall again below the reference voltage 52, so that the switch 43 is opened again. In order to prevent the switch 43 from switching too quickly, the comparator 51 can be provided with a hysteresis circuit.

The diode 41 can be part of the MOSFET which forms the switch 43.

The switch 44 for discharging the capacitor 40 is also designed as a MOSFET and is controlled in a similar manner as the switch 43. For this purpose, the voltage applied across the diode 41 is rectified via a diode rectifier 55 and applied to the negative input of a comparator 56. A fixed reference voltage 57 is applied to the positive input of the comparator 56. The output 58 of the comparator 56 is connected to the gate of the switch 44.

As long as HF current flows through the testing device, the output voltage of the diode rectifier 55 is higher than the reference voltage 57. If the electrosurgical generator now switches off the HF current, for example, in order to extinguish an unwanted spark, or during a no-pulse period in a pulsed operating mode, the output voltage of the diode rectifier 55 drops off and the comparator 56 switches. This closes the switch 44 and the capacitor 40 quickly discharges via the resistor 45.

An operating voltage for the comparators and the MOS-FETs can be obtained from the voltage across the capacitor 40 by means of a DC-DC converter (not depicted).

The invention claimed is:

1. Testing device for an electrosurgical generator, comprising:
   a first connection port and a second connection port for connecting the testing device to a patient circuit of the electrosurgical generator, the testing device being configured to physically detach from the electrosurgical generator, and
   a DC voltage source that is configured to generate a DC voltage through the first connection port and the second connection port,
   wherein an HF current path of the patient circuit runs from the first connection port to the second connection port through the testing device, and the a DC voltage source is fed by an HF current flowing through the HF current path.

2. Testing device according to claim 1, wherein DC source voltage comprises a capacitor arranged in the HF current path.

3. Testing device according to claim 2, wherein the DC voltage source is configured to conduct positive half-waves of the HF current through the capacitor and to not conduct negative half-waves of the HF current through the capacitor.

4. Testing device according to claim 3, wherein the DC voltage source has two parallel HF current paths, wherein a first HF current path comprises the capacitor and a first diode which is polarized in the direction of the positive half-waves of the HF current, and wherein a second HF current path has a second diode which is polarized in the direction of the negative half-waves of the HF current.

5. Testing device according to claim 4, wherein the first HF current path has a first switch for bridging the first diode.

6. Testing device according to claim 5, wherein the DC voltage source is configured to close the first switch when the DC voltage across the capacitor reaches a predetermined or predeterminable value.

7. Testing device according to claim 4, wherein the testing device has a device for discharging the capacitor.

8. Testing device according to claim 5, wherein the testing device has a device for discharging the capacitor.

9. Testing device according to claim 6, wherein the testing device has a device for discharging the capacitor.

10. Testing device according to claim 2, wherein the testing device has a device for discharging the capacitor.

11. Testing device according to claim 10, wherein the device for discharging the capacitor is configured to discharge the capacitor when no HF current flows through the HF current path.

12. Testing device according to claim 10, wherein the device for discharging the capacitor comprises a second switch.

13. Testing device according to claim 3, wherein the testing device has a device for discharging the capacitor.

* * * * *